Figure 1:
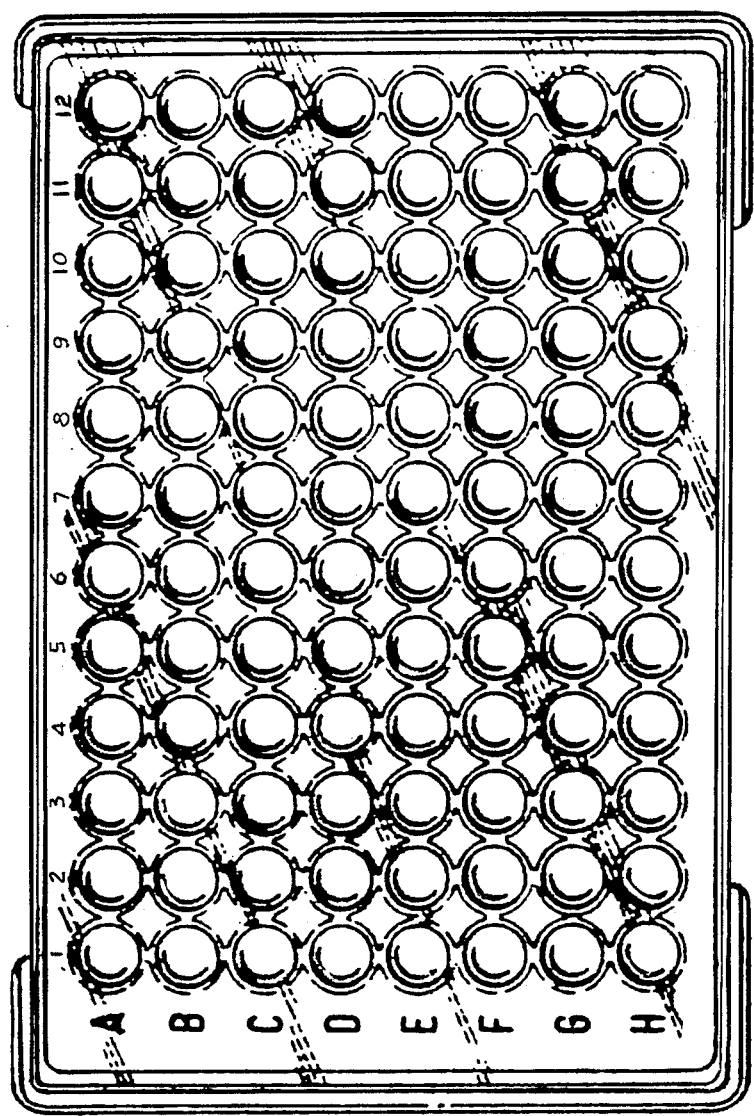

United States Patent [19]

Coleman

[11] Patent Number: 4,935,347

[45] Date of Patent: Jun. 19, 1990

[54] STABILIZATION OF COMPOUNDS

[75] Inventor: Michael H. Coleman, Putnoe, England

[73] Assignee: Radiometer Corporate Development Ltd., England

[21] Appl. No.: 124,351

[22] Filed: Nov. 23, 1987

Related U.S. Application Data

[63] Continuation of Ser. No. 941,508, Dec. 12, 1986, abandoned, which is a continuation of Ser. No. 686,922, Dec. 27, 1984, abandoned, which is a continuation of Ser. No. 289,072, Jul. 31, 1981, abandoned, which is a continuation of Ser. No. 163,002, Jun. 25, 1980, abandoned, which is a continuation of Ser. No. 897,457, Apr. 18, 1978, abandoned, which is a continuation of Ser. No. 757,411, Jan. 6, 1977, abandoned.

[30] Foreign Application Priority Data

Jan. 12, 1976 [GB] United Kingdom ............... 1021/76

[51] Int. Cl.$^5$ .................................................. C13Q 1/06
[52] U.S. Cl. ........................................ 435/29; 435/32; 435/39; 435/40

[58] Field of Search .................. 435/29, 32, 39, 40

[56] References Cited

U.S. PATENT DOCUMENTS

| | | | |
|---|---|---|---|
| 2,020,255 | 11/1935 | Copeman | 427/154 |
| 3,416,998 | 12/1968 | Streitfeld | 195/103.57 |
| 3,630,957 | 12/1971 | Rey | 252/408 |
| 3,713,985 | 1/1973 | Astle | 23/253 TP |
| 3,975,162 | 8/1976 | Renn | 23/253 TP |

Primary Examiner—Sam Siverberg
Attorney, Agent, or Firm—Ostrolenk, Faber, Gerb & Soffen

[57] ABSTRACT

A process for stabilizing compounds which comprises dispensing a solution of a film-forming material and the compound to be stabilized on a solid surface and allowing the solvent to evaporate to leave on the solid surface a quantity of material in the form of a thin coherent, dry flim adhering to said solid surface; and device for the application of said method and especially useful for performing biological tests.

23 Claims, 1 Drawing Sheet

STABILIZATION OF COMPOUNDS

This is a continuation of application Ser. No. 941,508, filed December 12, 1986, which was a continuation of application Ser. No. 686,922, filed December 27, 1984, which was a continuation of application Ser. No. 289,072 filed July 31, 1981, which was a continuation of application Ser. No. 163,002 filed June 25, 1980, which was a continuation of application Ser. No. 897,457, filed April 18, 1978, which was a continuation of application Ser. No. 757,411, of January 6, 1977, all of said prior applications now being abandoned.

The invention relates to a method for stabilising compounds, particularly biologically active compounds, and to a device useful for the application of said method and for performing biological tests.

It is commonly necessary for the identification of microorganisms to determine the effects of a variety of biologically active substances upon their growth. This is of particular importance in the case of antibiotic substances, where knowledge of the amount necessary to inhibit growth is needed for therapeutic application. The classical method for determining this minimum inhibitory concentration (MIC) is to prepare a series of tubes containing a liquid culture medium, with a different amount of anitbiotic in each tube. After inoculation with the microorganisms, and incubation the MIC can be determined from the tube with a lower antibiotic concentration, in which no growth has occured.

Alternative methods involve either preparing agar plates containing a series of antibiotic concentrations or plain agar plates into which the antibiotics are allowed to diffuse from paper discs impregnated with the antibiotics. All three methods require skill and considerable effort to perform and since some antibiotics are not stable in the culture medium the media require to be prepared freshly before use. Various methods have been proposed for reducing the effort of performing antibiotic sensibility tests.

U.S. Pat. No. 3,416,998 describes a process according to which several test compounds such as chemotherapeutical agents are mixed with a 1.5% aqueous solution of agar. The obtained mixture is poured on a plate to form a relatively thick layer which is then dried. The dried layers can be divided into smaller pieces containing a constant quantity of material per unit area of layer. Small discs of this material may be applied on bacterial cultures and the active agent is allowed to diffuse into the culture medium. The influence of the compound used on the growth of bacteria can subsequently be assessed. This method is however cumbersome and the results tend to vary considerably.

Dutch patent application No. 6917655 describes a method for assessing the growth and the physiology of bacteria by incorporating a chemical compound such as amino acids or other compounds which promote the growth of bacteria, into a solution of an inert high molecular material and adding this mixture in different tubes to obtain layers of material. In a later stage an inoculum is added and the growth is subsequently assessed. An aqueous solution of agar or a 1% solution of polyacrylamide are recommended as stabilisers for the chemical compound.

A disadvantage of the above method is that the deposited layer of chemical compound incorporated in the stabiliser is rather thick and has an insufficient mechanical stability. Another disadvantage is that a fairly big amount of stabiliser is used. In some instances this big proportion of stabiliser influences the composition and properties of the liquid in the tube.

The method involving the use of paper discs impregnated with anitbiotics is the subject of Dutch patent application No. 7205619 which involves the use of a paper disc as a carrier which is impregnated with an antibiotic which is placed on an agar plate. The antibiotic diffuses from the paper on the agar and produces a concentration gradient. Standardisation of this method gives problems and the obtained results vary considerably from one operator to another.

French patent specification No. 1,488,866 and Dutch patent application No. 7211868 describe a device for the determination of sensitivity of microorganisms in the presence of different antibiotics. The chemical compounds and the organism to be tested are present in lyophilised form which renders them sensitive to mechanical loss and leads to unreliable results.

There is thus a need for a simple economical and efficient method for stabilising very small quantities of accurately predispensed amounts of particularly biologically active substances in both mechanically and chemically stable form.

We have found a method for stabilising small amounts of biologically active substances which obviates to a great extent many of the difficulties previously encountered in the preparation of suitable systems for the determination of their effects on bacterial growth and which is compatible with known requirements for the satisfactory culture of microorganisms.

The process for stabilising compounds according to the invention involves:
(a) preparing a mixture comprising at least one component to be stabilised, a film-forming stabiliser and a solvent;
(b) dispensing a small proportion of the mixture upon a solid surface; and
(c) allowing the solvent to evaporate to give a coherent, dried film adhering to said solid surface and having a thickness not exceeding 50 microns.

By stabilisation is meant throughout the specification both a mechanical stabilisation and a chemical stabilisation for example against hydrolysis, pH- and ionic environment variations, high temperature etc.

The compound to be stabilised can be any compound, particularly biologically active compounds, such as antibiotics, which are sensitive to heat, presence of moisture, extreme pH conditions etc.

As stabiliser a wide range of materials with film-forming properties, can be used, such as agar, cellulosic derivatives or preferably proteinaceous materials like gelatin, casein, bovalbumin. For medical purposes gelatin is preferably used because
(a) it is an ampholyte with a good buffering capacity;
(b) it is reasonably soluble in relatively cold solution, which is a big advantage when dermolabile compounds are to be incorporated therein;
(c) it is a generally accepted microbiologically medium;
(d) it is a good film-forming material.

The solvent to be used can in principal be any solvent. For medical purposes distilled water is generally preferred for preparing aqueous solutions of the stabiliser and the compound to be stabilised. The preparation of such solutions and all subsequent steps are preferebly carried out below the temperature at which any of the components of the mixture would be affected.

The volume and concentration of the portions of the mixture of stabiliser and compound to be stabilised are chosen such that the material deposited on the solid surface yields after drying films of thickness not exceeding 50 microns. Suitable volumes and concentrations can easily be determined in each particular case to meet the requirements regarding thickness of the film, coherence and adherence to the solid surface.

Useful solutions of the stabiliser e.g. gelatin contain the stabiliser in a concentration which usually lies between 0.001 and 0.5% w/v, preferably between 0.01 and 0.1% w/v and particularly between 0.01 and 0.03% w/v.

When using a device as described further in the specification, volumes of 1 to 500 microliters, preferably 10 to 100 microliters of a solution of the mixture of stabiliser and compound to be stabilised are dispensed on the solid surface.

The solution to be dispensed is usually prepared by mixing appropriate volumes of the solutions of stabiliser and compound to be stabilised, if necessary adjusting the pH to the desired value, and where necessary sterilising.

In order to achieve the necessary mechanical stability i.e. good adherence to the solid surface after drying the films need to have a thickness from 0.01 to 50 microns, preferably from 0.01 to 5 microns, and ideally from 0.3 to 1 micron. It is important that the dried films are of a thickness within the given range, since contraction of thicker films during drying causes detachment at the edges and loss of mechanical stability.

To some extent the adherence of the films depends on the geometry of the solid surface on which the mixture is dispensed.

There seems little or no difference in the behavior of the obtained thin films towards different synthetic plastic materials such as polyethylene, polystyrene, polycarbonate, polyvinylchloride, polymethacrylate or polytetrafluorethylene.

The drying procedure requires also some attention. Useful dried films are formed by removing the solvent which can be any solvent but is usually water, by airdrying or preferably under reduced pressure. It is preferred that the drying is carried out under such conditions that the liquid does not boil or freeze since boiling can give rise to mechanical loss, and freeze-drying does not yield a coherent film. In the case of water as a solvent, the liquid is preferably kept between 5° to 30° C. and the vacuum around 20 Torr.

A very useful application of the above described method for stabilising compounds is the production of a device useful for performing biological tests, particularly the determination of the minimum inhibitory concentration of antibiotics against pathogenic microorganisms. A useful device to be used for such determinations consists of an array of several rows of wells containing a coherent, dry film of a thickness not exceeding 50 microns, of at least one compound to be stabilised, incorporated in a film-forming stabiliser, adhering to the inner surface of the wells.

The compound to be stabilised can be any compound, especially a biologically active compound such as an antibiotic.

The stabilisation can be any film-forming substance. When used for medical purposes a proteinaceous material such as gelatin or serum boval bumine is preferred.

The wells can contain the same or different compounds in the same concentration or in predetermined concentrations varying from well to well.

The films are prepared following the procedure described above. The device can be sealed with an adhering foil and may be stored at ambient temperatures for several months until required for use.

The device can be made of any material. A synthetic material like polystyrene is particularly suitable.

A preferred embodiment of the device consists of rectangular plates of approximately 12×8×1.5 cm, each containing an array of 8 rows of 12 circular wells, 0.5 in diameter and 1 cm deep, having hemispherical bottoms (see FIG. 1). Dilutions of any chemical compound to be tested in solution with the stabiliser are dispensed in the first 10 wells of the row, the last 2 wells receiving aliquots of the stabilising solution only. The volume, concentration of the stabiliser and the chemical compound and the surface area on which the solution is dispensed are chosen such that after drying films of a thickness from 0.01 to 50 microns, preferably from 0.01 to 5 microns and ideally from 0.3 to 1 micron, are formed e.g. on the bottom of the wells.

After addition of the mixture of stabiliser and the chemical compound to be tested and drying by air or vacuum drying the device can be covered with an adhering foil or laminate and sealed, to protect it from its environment.

The above illustrates the use of the invention for stabilising biologically active compounds. It is understood that the invention covers stabilising any substance if necessary by applying obvious variations of the above method.

The invention will be further illustrated by the following Examples.

EXAMPLE I

Solutions of the antibiotics listed, to the concentration indicated, were prepared in distilled water at room temperature:

| | |
|---|---|
| Sulphamethoxazole | 200 µg/ml |
| Trimethoprim | 40 µg/ml |
| Benzyl penicillin | 12 µg/ml |
| Ampicillin | 80 µg/ml |
| Cephaloridine | 80 µg/ml |
| Tetracycline | 80 µg/ml |
| Erythromycin | 80 µg/ml |
| Gentamicin | 80 µg/ml |

The solutions were sterilised in the cold by passing through a suitable filter, and each was diluted with an equal volume of a 0.05% w/v solution of good grade gelatin (200 bloom number) in distilled water at room temperature, which had previously been adjusted to pH 7 and sterilised in an autoclave for 15 minutes at 15 lbs pressure. From each such antibiotic solution a further series of nine doubling dilutions were prepared aseptically, by successive dilutions with equal volumes of a 0.025% w/v solution of gelatin, previously adjusted to pH 7 and sterilised by autoclaving.

These solutions were then transferred to the sterile reservoirs of a device (U.K. Pending Patent Application No. 44,493/74) capable of dispensing 96 drops, each of 25 µl volume, into the wells of a polystyrene plate. The plates used were rectangular in shape approximately 12×8×1.5 cm; each containing an array of 8 rows of 12 circular wells, 0.5 cm in diameter and 1 cm deep, having hemispherical bottoms. The dilutions of each antibiotic were dispensed into the first 10 wells of a row, the last two wells receiving 25 μl aliquots of 0.025% w/v gelatin solution only.

The plates so prepared were vacuum-dried by ensuring that the vacuum did not fall below 20 Torr, nor the temperature rise substantially above ambient temperature. The thickness of the obtained films was about 0.4 microns. The plates were sealed with a laminate of aluminum foil in a heat sealing device (from Sharp-Intermatic or Aylesham, U.K.).

Plates so prepared were examined for antibiotic potencies by the addition of a 50 μl aliquot of a suitable bacteriological culture broth, containing approximately $10^6$ microorganisms per ml. Various culture broths have been employed, but the one principally used is the heart-infusions broth (from Difco Laboratories of Detroit, U.S.). Two microorganisms have been used in most of the tests, Staph. aureus NCTC 6572 and E. coli NCTC 10418. The plates were then resealed with a suitable adhesive film (from Cellotape Products UK of Middlesex, U.K.) and incubated at 37° C. overnight. The minimum inhibitory concentration (MIC) of each of the antibiotics was then determined by inspection of the plates, and noting the lowest concentration at which no growth was apparent. Growth was indicated by a button of cells at the bottom of the wells. For control purposes the penultimate well of each row received a 50 l aliquot of the culture broth without organisms, and should remain free of growth after incubation; whilst the last well of each row, having received an inoculum of organisms, but no antibiotic substance should give good growth throughout. No defects in the procedure have been indicated by these two control columns in any of the plates examined.

No loss of potency in the antibiotics tested has been observed over a period of 3 months whether stored at −20° C., 2° C. or 20° C., whereas the penicillins in particular show a rapid loss of potency when dried without the stabiliser, and stored at ambient temperatures.

EXAMPLE II

The procedure of Example I was followed with the exception that 25 μl of an aqueous solution of 0.075% w/v of gelatin was used. The thickness of the obtained film was about 1 micron.

EXAMPLE III

The procedure of Example I was followed with the exception that 25 μl of an aqueous solution of 0.0075% w/v gelatin was used. The thickness of the film obtained was about 0.1 micron.

EXAMPLE IV

The procedure of Example I was followed with the exception that 25 μl of an aqueous solution of 0.025% w/v bovine serum albumine was used. The thickness of the film obtained was about 0.4 microns.

The product obtained according to Examples II–IV displayed the same outstanding properties as the product according to Example I.

I claim:

1. An improved device for carrying out a biological test, said device comprising a plate having a plurality of wells therein and a mechanically and chemically stabilized biologically active test compound located in said wells, said compound being located in said wells in a dry form compatible with requirements for the culture of microorganisms and constituting a part of a coherent dry film having a thickness of 0.01 to 5 microns, said film being adherent to the inner surface of its respective well and said film including a water-soluble polymeric film-forming substance in addition to said biologically active compound so that said compound is held in said wells in mechanically and chemically stabilized form.

2. The device of claim 1 made by the process in which an aqueous solution of said film-forming substance containing said biologically active compound is dispensed into the wells of said plate in an amount sufficient for said film to have a thickness in the range of 0.01 to 5 microns and the water is evaporated at a temperature and pressure such that the liquid does not freeze or boil while forming said film.

3. The device of claim 2 in which said pressure is a reduced pressure.

4. The device of claim 2 in which the dispensing is in an amount sufficient for the film to have a thickness in the range of 0.3 to 1 micron.

5. The device of claim 2 in which the film-forming substance is a proteinaceous substance.

6. The device of claim 2 in which the film-forming substance is gelatine or bovine serum albumin.

7. The device of claim 2 covered by an adhering foil.

8. The device according to claim 1, in which the thickness of the film varies from 0.3 to 1 micron.

9. The device according to claim 1, wherein the stabiliser is a proteinaceous substance.

10. The device according to claim 9, wherein the stabiliser is gelatin.

11. The device according to claim 9, wherein the stabiliser is bovine serum albumine.

12. The device according to claim 1, wherein the compound to be stabilised is an antibiotic.

13. The device according to claim 1, in which the wells contain films containing the same or different compounds present in the same or in predetermined concentrations varying from well to well.

14. Apparatus according to claim 1 covered by an adhering foil.

15. The device of claim 3 covered by an adhering foil.

16. The device of claim 2 in which the biologically active compound is an antibiotic.

17. In a method for the testing of microorganisms in a liquid medium, the improvement which comprises dispensing a bacterial culture broth containing microorganisms into at least one well of a plate having a plurality of wells therein and a mechanically and chemically stabilized biologically active test compound located in said wells, said compound being located in said wells in a dry form compatible with requirements for the culture of microorganisms and constituting a part of a coherent dry film having a thickness of 0.01 to 5 microns, said film being adherent to the inner surface of the respective wells and said film including a water soluble polymeric film-forming substance in addition to said biologically active compound so that the compound is held in said wells in a mechanically and chemically stabilized form, and the plate is incubated.

18. The method of claim 17 in which said film has a thickness in the range of 0.3 to 1 micron.

19. The method of claim 17 in which the film-forming substance is a protinaceous substance.

20. The method of claim 17 in which the film-forming substance is gelatine or bovine serum albumin.

21. The method of claim 17 in which the biologically active test compound is an antibiotic.

22. The method of claim 17 in which the minimum inhibitory concentration of said antibiotic is determined.

23. The method of claim 17 in which at least two wells of said plurality of wells contain at least one of different concentrations of the same biologically active test compound or different biologically active test compounds.

* * * * *